(12) United States Patent
Butters et al.

(10) Patent No.: US 7,307,174 B2
(45) Date of Patent: Dec. 11, 2007

(54) PROCESS AND INTERMEDIATES FOR THE PREPARATION OF THIENOPYRROLE DERIVATIVES

(75) Inventors: Michael Butters, Bristol (GB); Paul Schofield, Macclesfield (GB); Andrew Stocker, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 178 days.

(21) Appl. No.: 10/528,612

(22) PCT Filed: Sep. 29, 2003

(86) PCT No.: PCT/GB03/04211

§ 371 (c)(1),
(2), (4) Date: Mar. 21, 2005

(87) PCT Pub. No.: WO2004/031193

PCT Pub. Date: Apr. 15, 2004

(65) Prior Publication Data

US 2005/0272938 A1    Dec. 8, 2005

(30) Foreign Application Priority Data

Oct. 3, 2002   (GB) .................. 0222909.4

(51) Int. Cl.
C07D 495/04 (2006.01)
(52) U.S. Cl. .................................. 548/453
(58) Field of Classification Search ................ 548/453
See application file for complete search history.

(56) References Cited

U.S. PATENT DOCUMENTS

| 2004/0048878 A1 | 3/2004 | Cai et al. |
| 2004/0142938 A1 | 7/2004 | Sher et al. |
| 2004/0220229 A1 | 11/2004 | Bussolotti et al. |

FOREIGN PATENT DOCUMENTS

| EP | 1088824 A2 | 4/2001 |
| EP | 1136071 A3 | 3/2003 |
| EP | 1 340 500 A1 | 9/2003 |
| JP | 2004196702 A | 7/2004 |
| WO | WO-94/18196 A | 8/1994 |
| WO | WO-94/18196 A1 | 8/1994 |
| WO | WO-01/28993 A2 | 4/2001 |
| WO | 01/32622 A1 | 5/2001 |
| WO | WO-02/06246 A | 1/2002 |
| WO | WO-02/06246 A1 | 1/2002 |
| WO | WO-02/20530 A1 | 3/2002 |
| WO | 03/072570 A1 | 9/2003 |
| WO | WO-03/074484 A1 | 9/2003 |
| WO | WO-03/074485 A2 | 9/2003 |
| WO | WO-03/074513 A2 | 9/2003 |
| WO | WO-03/074517 A1 | 9/2003 |
| WO | WO-03/074531 A1 | 9/2003 |
| WO | WO-03/074532 A1 | 9/2003 |
| WO | WO-03/091213 A1 | 11/2003 |
| WO | 2004/031194 A1 | 4/2004 |
| WO | WO-2004/041780 A2 | 5/2004 |
| WO | WO-2004/058715 A1 | 7/2004 |
| WO | 2004/092158 A1 | 10/2004 |
| WO | WO-2004/113345 A1 | 12/2004 |
| WO | 2005/013975 A1 | 2/2005 |
| WO | 2005/013981 A1 | 2/2005 |
| WO | 2005/018637 A1 | 3/2005 |
| WO | 2005/019172 A1 | 3/2005 |
| WO | 2005/020985 A1 | 3/2005 |
| WO | 2005/020986 A1 | 3/2005 |
| WO | 2005/020987 A1 | 3/2005 |

OTHER PUBLICATIONS

Redman, et al., Bioorganic & Medicinal Chemistry Letters 11(1) (2001), pp. 9-12.*
Adams et al., "4-Amino-4,5-dihydrothiophene-2-carboxylic acid," J. Org. Chem. 50:2730-2736 (1985).
Binder et al., "Eine einfache herstellungsmethode fur 2-aminothiophene," Synthesis Communications 4:255-256 (1977).
Binder et al., "Thiopen als strukturelement physiologisch aktiver substanzen, 8. mitt. 1H5H-imidazo[1,2-a]thieno[3,4-d]pyrimidin-2(3H-one," Arch Pharm. 314:556-564 (1981).
Bjork et al., "Improved syntheses of thieno[2,3-*b*]- and [3,2-*b*]-fused naphthyridines," J. Heterocyclic Chem. 32:751-754 (1995).

(Continued)

*Primary Examiner*—Kamal A. Saeed
*Assistant Examiner*—Michael P. Barker

(57) ABSTRACT

Novel Process and Intermediates. A process for preparing a compound of formula (I) where $R^4$ and $R^5$ are as defined in the specification; and $R^6$ is hydrogen or a protecting group, which process comprises cyclisation of a compound of formula (II) where $R^4$ and $R^5$ and $R^6$ are as defined in relation to formula (I), and $R^7$ is nitrogen protecting group, and removing the group $R^7$, and thereafter if desired, removing any protecting group $R^6$. Novel intermediates and the use of these in the formation of pharmaceutical compounds is also described and claimed

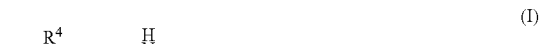

(I)

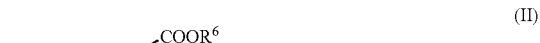

(II)

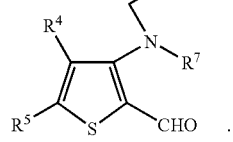

3 Claims, No Drawings

OTHER PUBLICATIONS

Boger et al., "Total synthesis of distamycin A and 2640 analogues: A solution-phase combinatorial approach to the discovery of new, bioactive DNA binding agents and development of a rapid, high-throughput screen for determining relative DNA binding affinity or DNA binding sequence selectivity," J. Am. Chem. Soc. 122:6382-6394 (2000).

Brugier et al., "α-Substitution of β-thienylcarbamates: alkylation, vinylation and Pd-catalyzed coupling reactions," Tetrahedron 56:2985-2993 (2000).

Brugier et al., "Studies on the reactivity of N-(3-thienyl)carbamates," J. Chem. Soc., Perkin Trans. 1:37-43 (2001).

Brugier et al., "Synthesis and reactivity of alkyl (4-aminothien-3-yl)carbamates," Tetrahedron 53(30):10331-10344 (1997).

Brunnett et al., "Heterocyclic amines. IV. Urethan and urea derivatives of 3-aminothiophene (1)," J. Heterocyclic Chem. 5(3):417-418 (1968).

Carroll et al., "Competitive ortho metalation effects: the kinetic and thermodynamic lithiation of 3-(*tert*-Butoxycarbonyl)amino-4-caromethoxythiopene," Tetrahedron Letters 38(15):2637-2640 (1997).

Eras et al., "Reactivity of thienopyrroles. synthesis of isomeric nitro and bromothienopyrroles," J. Heterocyclic Chem. 21:215-217 (1984).

Galvez et al., "Synthesis of isomeric β-haloethylthienopyrroles," J. heterocyclic Chem., 21, 393-395 (1984).

Galvez et al., "Synthesis of thiophenedicarbonyldiazides and Di-*t*-butyl thiophendicarbamates," J. Heterocyclic Chem. 23:1103-1108 (1986).

Jones et al., "The vilsmeier reaction of fully conjugated carbocycles and heterocycles," Organic Reactions 49:1-39 (1997).

Kobayashi et al., "Heterocyclic sulfonyl compounds and activated blood coagulation factor X (FXa) inhibitors containing them," Chemical Abstracts XP002267904 & JP 2001 294572 (2001).

Linda et al., "The mechanism of the Vilsmeier-Haach reaction. Part III. Structural and solvent effects," J. Chem. Soc. Perkins Trans II, 1610-1612 (1974).

Marques et al., "Toward an understanding of the chemical etiology for DNA minor-groove recognition by polyamides," Helvetica Chimica acta 85:4485-4517 (2002).

Martin et al., "Nuclear magnetic resonance investigations of carbonium ion intermediates. Part II. Exchange reactions in chloroiminium salts (Vilsmeier-Haack reagents)," Journal Chem. Soc., Perkins Trans II 642-646 (1974).

Martin et al., "Recherches sur la reaction de vilsmeier-haack etude du mecanisme de formation du complexe par des mesures cinetiques en resonance magnetique nucleaire," Tetrahedron Letters 58:5061-5064 (1970).

Meth-Cohn et al., "A versatile new synthesis of quinolines and related fused pyridines. Part II.," Tetrahedron Letters 33:3111-3114 (1979).

Meth-Cohn et al., "A versatile new synthesis of quinolines and related fuses pyridines. Part 7. The conversion of acetamidothiophens into thienopyridines,"Journal Chem. Soc., Perkins Trans. I 1531-1536 (1981).

Meth-Cohn et al., "A versatile new synthesis of quinolines, thienopyridines and related fused pyridines," Tetrahedron Letters 23:2045-2048 (1978).

Meth-Cohn et al., "The preparation and formylation of 2-acetamidothiophenes," Synthesis 2:133-135 (1980).

Nakamura, "Construction of heterocyclic compounds by use of alpha-diazaphosphonates: new one-pot syntheses of indoles and isocoumarines," Organic Letters 4(14)2317-2320 (2002).

Rajanna et al., "Kinetics adn mechansim of vilemeier-haach synthesis of 3-formyl chromones derived from o-hydroxy aryl alkyl ketones: A structure reactivity study," Tetrahedron 52(10):3669-3682 (1996).

Seela et al., "168. Synthesis of 2'-deoxyribofuranosides of B-Aza-7-deazaguanine and related pyrazolo[3,4-*d*]pyrimidines," Helvetica Chimica Acta 69:1602-1613 (1986).

Shinkwin et al., "Synthesis of thiophenecarboxamides, thieno[3,4-*c*]pyridin-4(5*H*)-ones and Thieno[3,4-*d*]pyrimidin-4(3*H*)-ones and preliminary evaluation as inhibitors of poly(ADP-ribose)polymerase (PARP)," Bioorganic & Medicinal Chemistry 7:297-308 (1999).

Shvedov et al., 2-Aminothieno '2,3-b]pyridine derivatives, Chemical Abstracts, XP002266826 & SU364613 (1973).

Soth et al., "Recherches en serie heterocyclique. XXIX. Sur des voies d'acces a des thieno, selenolo, furo et pyrrolopyrroles," Canadian Journal of Chemistry 56(6):1429-1434 (1978).

Stanetty et al., "Herbizide thienylharnstoffe, I," Monatshefte fur Chemie 120:53-63 (1989).

Sugiyama et al., "Condensed thienopyrimidines. IV. Synthesis and gastric antisecretory activity of 2,3-dihydro-5H-oxazolothienopyrimidine derivatives," Chemical & Pharmaceutical Bulletin 37(10):2171-2722 (1989).

Sugiyama et al., "Condensed thienopyrimidines. 5. Studies on the thermal cyclization of various ortho-formylthiophenecarbamates with ethanolamine," Heterocycles 29(7):1317-1323 (1989).

Szabo et al, "Experimental and theoretical study of orientation in the nitration of dithieno[3,4-b:3',4'-d]pyridine," J. Organic Chem 56:1590-1596 (1991).

Adams et al., "4-Amino-4,5-dihydrothiophene-2-carboxylic acid," Journal of Organic Chemistry 50(15):2730-2736 (1985).

Binder et al., "Thiophen als a Strukturelement physiologisch aktiver substanzen, 8. Mitt. 1H, 5H-Imidazo '1,2-althieno'3,4-dlpyrimidin,—2(3H)-one," Archiv der Pharmazie 314(6):556-564 (1981).

Bjoerk et al., "Improved systhesis of thieno '2,3-bl-and '3,2-bl-fused naphthyridines," Journal of Heterocyclic Chemistry 32(3):751-754 (1995).

Boger et al., "Total synthesis of distamycin A and 2640 analogs: A solution-phase cmbinatorial approach to the discovery of new, bioactive DNA binding agents and development of a rapid high-throughput screen for determining relative DNA binding affinity or DNA binding sequence selectivity," Journal of the American Chemical Society 122(27):6382-6394 (2000).

Brugier et al., ".alpha.-substituteion of .beta.-thienylcarbamates: alkylation, vinylation and Pd-catalyzed coupling reactions," Tetrahedron 56(19):2985-2993 (2000).

Brugier et al., "Synthesis and ractivity of alkyl (4-amino-3-thienyl)carbamates," Tetrahedron 53(30):10331-10344 (1997).

Brugier et al., "Studies on the reactivity of N-(3-thienyl)carbamates," Journal of the Chemical Society, Perkin Transactions 1 1:37-43 (2001).

Brunnett et al., "Heterocyclic amines. IV. Urethan and urea derivatives of 3-aminothiophene," Journal of Heterocyclic Chemistry 5(3):417-418 (1968).

Carroll et al., "Competitive ortho metalation effects: the kinetic and thermodynamic lithiation of 3-(tert-butoxycarbonyl)amino-4-carbomethox ythiophene," Tetrahedron Letters 38(15):2637-2640 (1997).

Galvez et al., "Synthesis of isomeric.beta.-haloethylthienopyrroles," Journal of Heterocyclic Chemistry 21(2):393-395 (1984).

Galvez et al., "Synthesis of thiophenedicarbonyldiazides and di-t-butyl thiophendicarbamates," Journal of Heterocyclic Chemistry 23:1103-1108 (1986).

Kobayashi et al., "Heterocyclic sulfonyl compounds and activated blood coagulation factur X (FXa) inhibitors containing them," Database CA 'online! Chemical Abstracts Service, Database accession No. 135:313616 XP002267904 368442-47-1 and JP 2001 294572 A (2001).

Marques et al., "Toward an understanding of the chemical etiology for DNA minor-groove recognition by polyamides," Helvetica Chimica Acta 85(12):4485-4517 (2002).

Shinkwin et al., "Synthesis of thiophenecarboxamides, thieno '3,4-clpyridiin-4(5H)-ones and thieno '3,4-dlpyrimidin-4(3H)-ones and preliminary evaluation as inhibitors of poly(ADP-ribose)polymerase (PARP)," Bioorganic & Medicinal Chemistry 7(2):297-308 (1999).

Szabo et al., "Experimental and theoretical study in orientation in the nitration of dithieno '3,4-d:3',4'-dlpyridine," Journal of Organic chemistry 56(4):1590-1596 (1991).

Freeman, S., et al., "Effect of Glucose on Rat and Human Liver Glycogen Phosphorylasea Activity and Potency of a Glycogen Phosphoylase Inhibitor," Diabetes, 52, Supp., 1470-P, A340 (2003).

Turnbull, A., et al., "Pharmacological Inhibition of Glycogen Phosphorylase (GP) Lowers Plasma Glucose in Rat Models of Type 2 Diabetes," Diabetes, 52, Suppl., 1485-P, A343 (2003).

Hudson, S., et al., "The effect of a glycogen phosphorylase inhibitor upon muscle fatigue in anaesthetised rats," J. Physiol., 539:52-53 (2002).

Vertigan, H. et al. "Impact of cell glycogen content on modulation of hepatocyte glucose metabolism by pharmacological agents", EASD Munich (2004).

Bartlett, J. et al. "In Vitro and In Vivo Profile of Gpi688, a Novel, Potent Inhibitor of Glycogen Phosphorylase", ADA San Diego (2005).

Simpson, I. et al. "Novel Orally Active Amino-indan Inhibitors of Glycogen Phosphorylase", Cambridge Med Chem Conference, (Sep. 2005). Poster EOM.

Green, A R. et al. "The Glycogenic Action of Protein Targeting to Glycogen in Hepatocytes Involves Multiple Mechanisms Including Phosphorylase Inactivation and Glycogen Synthase Translocation", J Biol Chem, 279(45), 46474-46482 (2004).

Roberts, P A. et al. "The temporal relationship between glycogen phosphorylase and activation of the pyruvate dehydrogenase complex during adrenaline infusion in resting canine skeletal muscle", J Physiology-London 545(1), 297-304 (2002).

* cited by examiner

PROCESS AND INTERMEDIATES FOR THE PREPARATION OF THIENOPYRROLE DERIVATIVES

RELATED APPLICATIONS

This application is a national stage filing under 35 U.S.C. 371 of International Application PCT/GB2003/004211, filed Sep. 29, 2003, which claims priority from United Kingdom Patent Applications No. 0222909.4, filed Oct. 3, 2002, the specifications of each of which are incorporated by reference herein. International Application PCT/GB2003/004211 was published under PCT Article 21(2) in English.

The present invention relates to a novel process for preparing intermediates for therapeutically effective compounds, together with novel intermediates for use in the process.

Compounds with glycogen phosphorylase activity are described in WO 02/20530. These compounds have a general formula which may be represented as formula (A)

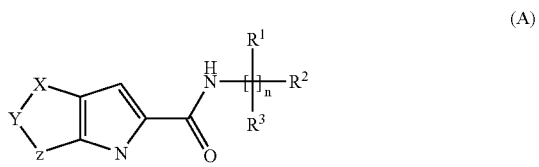

where X, Y and Z is selected from inter alia —S—$CR^4$=$CR^5$—, $R^4$ and $R^5$ are independently selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N-($C_{1-6}$alkyl)sulphalnoyl, N,N,-($C_{1-6}$alkyl)$_2$sulphamoyl, $C_{1-6}$alkylsulphonylamino and $C_{1-6}$alkylsulphonyl-N-($C_{1-6}$alkyl)amino;

n is 0-4, and $R^1$, $R^2$ and $R^3$ are various specified organic groups.

These compounds are generally prepared by a reacting an acid of formula (B)

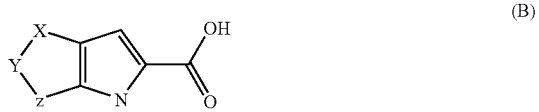

with an appropriate amine. Acids of formula (B) are prepared according to the following scheme:

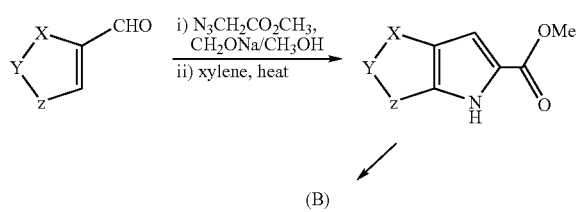

However, this process is difficult to effect as it may proceed explosively.

The applicants have found an improved process for the production of certain intermediates.

The present invention provides a process for preparing a compound of formula (I)

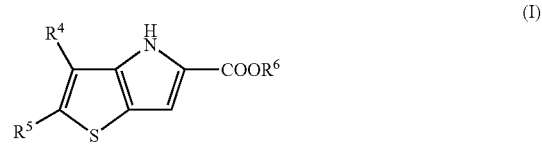

where $R^4$ and $R^5$ are independently selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$-alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$-alkanoylamino, N-($C_{1-6}$alkyl)carbamoyl, N,N-($C_{1-6}$alkyl)$_2$carbamoyl, $C_{1-6}$-alkylS(O)$_a$ wherein a is 0 to 2, $C_{1-6}$alkoxycarbonyl, $C_{1-6}$-alkoxycarbonylamino, N-($C_{1-6}$alkyl)sulphamoyl, N,N,-($C_{1-6}$alkyl)$_2$sulphamoyl, $C_{1-6}$alkylsulphonylamino and $C_{1-6}$alkylsulphonyl-N-($C_{1-6}$alkyl)amino; and $R^6$ is hydrogen or a protecting group, which process comprises cyclisation of a compound of formula (II)

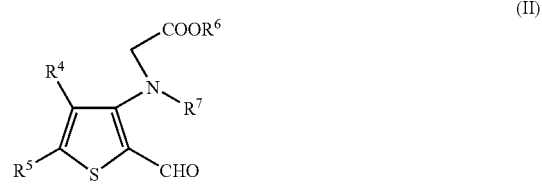

where $R^4$, $R^5$ and $R^6$ are as defined in relation to formula (I), and $R^7$ is a nitrogen-protecting group, and removing the group $R^7$, and thereafter if desired, removing any protecting group $R^6$.

Cyclisation is suitably effected in an organic solvent such as dimethylformamide (DMF), N-methylpyrrolidone or dimethylacetamide, in the presence of a base, preferably a weak base such as an alkali metal carbonate or bicarbonate, such as potassium carbonate. The reaction is suitably carried out at elevated temperatures, for example of from 40 to 100° C., and preferably at about 60° C. Under these conditions, $R^7$ is generally removed in the same reaction step. Depending upon the nature of the group employed however, it might be necessary to remove $R^7$ in a subsequent step, for example by acid or base hydrolysis reactions.

Acid hydrolysis reactions may be carried out using conventional methods, and in particular using acids such as trifluoromethanesulphonic acid, acetic acid or hydrochloric acid. Base hydrolysis reactions are suitably effected in the presence of bases, such as alkali metal hydrides or hydroxides, and in particular sodium or potassium hydroxide.

Suitable example of protecting groups $R^7$ are listed in T.W. Green, Protecting Groups in Organic Synthesis, J. Wiley and Sons, 1991 and in particular are those designated as nitrogen protection groups.

Particular examples of protecting groups $R^7$ are groups of sub-formula (i)

where $R^8$ is a hydrocarbyl or heterocyclic group, either of which may be optionally substituted.

As used herein, the expression "hydrocarbyl" includes any structure comprising carbon and hydrogen atoms. For example, these may be alkyl, alkenyl, alkynyl, aryl such as phenyl or napthyl, arylalkyl such as benzyl, or cycloalkyl, cycloalkenyl or cycloalkynyl. Suitably hydrocarbyl groups contain up to 20 and preferably up to 10 carbon atoms.

The term "aryl" refers to aromatic rings such as phenyl or naphthyl.

The term "heterocyclic" includes aromatic or non-aromatic rings, for example containing from 4 to 20, suitably from 5 to 8 ring atoms, at least one of which, and suitably from 1 to 4 of which is a heteroatom such as oxygen, sulphur or nitrogen. They may be monocyclic or have fused rings, such a bicyclic or tricyclic ring systems. Examples of such groups include furyl, thienyl, pyrrolyl, pyrrolidinyl, imidazolyl, triazolyl, thiazolyl, tetrazolyl, oxazolyl, isoxazolyl, piperidinyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

The term "heteroaryl" refers to heterocyclic groups which are aromatic in nature. Thus these may comprises cyclic aromatic hydrocarbons in which one or more carbon atoins have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quniolizinyl, isoquinolyl, quinolyl phthalazinyl, naphthyridinyl, quinoxalinyl, isothiazolyl and benzo[b]thienyl. Preferred heteroaryl groups are five or six membered rings and contain from one to three heteroatoms.

Suitable optional substituents for heterocyclic and hydrocarbyl groups $R^8$ include nitro, cyano, halo, oxo, =$CR^{13}R^{14}$, $C(O)_xR^{12}$, $OR^{12}$, $S(O)_yR^{12}$, $NR^{13}R^{14}$, $C(O)NR^{13}R^{14}$, $OC(O)NR^{13}R^{14}$, =$NOR^{12}$, —$NR^{12}C(O)_xR^{13}$, —$NR^{12}CONR^{13}R^{14}$, —N=$CR^{13}R^{14}$, $S(O)_yNR^{13}R^{14}$ or —$NR^{12}S(O)_yR^{13}$ where $R^{12}$, $R^{13}$ and $R^{14}$ are independently selected from hydrogen or optionally substituted hydrocarbyl, or $R^{13}$ and $R^{14}$ together form an optionally substituted ring which optionally contains further heteroatoms such as $S(O)_y$, oxygen and nitrogen, x is an integer of 1 or 2, y is 0 or an integer of 1-3. Hydrocarbyl groups $R^8$ may also include heterocyclic substituents, which may themselves be optionally substituted by one or more of the optional substituents listed above. Heterocyclic groups may also be substituted with hydrocarbyl groups which may also be optionally substituted by any of the groups listed above.

Preferably $R^8$ is a hydrocarbyl group such as alkyl, aryl or arylalkyl. Most preferably $R^8$ is a straight chain alkyl group of from 1 to 6 carbon atoms, and particularly is a straight chain $C_{1-4}$alkyl group, such as methyl.

Examples of protecting groups $R^7$ are groups of sub-formula (i)

where $R^8$ is a straight chain alkyl group of from 1 to 6 carbon atoms, and particularly is a straight chain $C_{1-4}$alkyl group, such as methyl.

Particular examples of ester protecting groups $R^6$ are any organic groups which can be removed by hydrogenation or hydrolysis. These include optionally substituted hydrocarbyl or optionally substituted heterocyclic groups. Such groups may be similar to those listed above in relation to $R^7$.

Suitable example of protecting groups $R^6$ are also listed in T.W. Green, Protecting Groups in Organic Synthesis, J. Wiley and Sons, 1991 and in particular are those designated as acid protecting groups.

In particular $R^6$ is a hydrocarbyl group such as $C_{1-6}$alkyl, $C_{2-6}$alkenyl, $C_{2-6}$alkynyl, aryl such as phenyl, or arylalkyl such as benzyl.

Conversion of a protecting group $R^6$ to hydrogen is suitably effected using conventional methods, for example as described in WO 02/20530. In particular, the compound is reacted with a base such as lithium hydroxide, in an organic solvent such as methanol, at temperatures of from 20-80° C., and conveniently at the reflux temperature of the solvent.

Particular examples of groups $R^4$ and $R^5$ are hydrogen, halo, nitro, cyano, fluoromethyl, difluoromethyl, trifluoromethyl, trifluoromethoxy, carboxy, carbamoyl, sulphamoyl, ureido, $C_{1-6}$-alkyl, $C_{2-6}$alkenyl, $C_{2-6}$alkynyl, $C_{1-6}$-alkoxy, $C_{1-6}$alkanoyl and $C_{1-6}$alkanoyloxy.

Suitably $R^4$ and $R^5$ are independently selected from hydrogen, halo, nitro, cyano, fluoromethyl, difluoromethyl, trifluoromethyl, trifluoromethoxy, carboxy, carbamoyl, sulphamoyl, $C_{1-4}$alkyl, $C_{2-4}$alkenyl, $C_{2-4}$alkynyl, $C_{1-4}$alkoxy, $C_{1-4}$alkanoyl, and $C_{1-4}$alkanoyloxy.

Preferably $R^4$ and $R^5$ are independently selected from hydrogen and halo such as chloro, fluoro and bromo, and in particular chloro.

Most preferably $R^4$ and $R^5$ are halo such as chloro.

Compounds of formula (II) are suitably prepared by reacting a compound of formula (III)

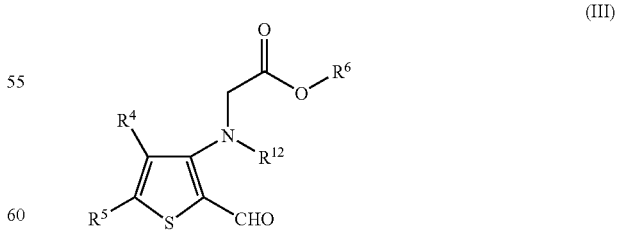

where $R^4$, $R^5$ and $R^6$ are as defined in relation to formula (I), and $R^{12}$ is a directing nitrogen-protecting group, with a compound of formula (IV)

$(R^7)_2O$            (IV)

where $R^7$ is as defined above, under acidic condition, for example in a solvent comprising an organic acid, such as acetic acid. Elevated temperatures for example of from 80-150° C. and preferably from 110-130° C. are employed.

Directing nitrogen protecting groups are groups which may act as nitrogen protecting groups, but are sufficiently bulky in nature to prevent any substitution on the nitrogen atom, or the ring atom to which it is attached. Reactions, for example deprotonation by an organolithium reagent, are thereby directed to the adjacent position on the ring. Thus particular examples of nitrogen directing groups $R^{12}$ are groups of sub-formula (ii)

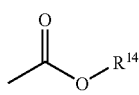

(ii)

where $R^{14}$ is a branched $C_{4-10}$alkyl group such as tertiary butyl, or an aryl or $C_{1-4}$alkylaryl group such as benzyl.

Compounds of formula (III) are suitably prepared by reacting a compound of formula (V)

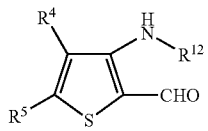

(V)

where $R^4$ and $R^5$ are as defined above in relation to formula (I) and $R^{12}$ is as defined in relation to formula (III), with a compound of formula (VI)

$$LCH_2COOR^6 \quad (VI)$$

where L is a leaving group such as halogen and in particular bromine. The reaction is suitably effected in the presence of a base such as an alkali metal carbonate, bicarbonate, hydroxide or alkoxide, for instance potassium bicarbonate in an organic solvent such as dimethylformamide. The reaction may be conducted at elevated temperatures, for example of from 40 to 100° C., preferably from 50 to 70° C. and most preferably at about 60° C.

Compounds of formula (V) are suitably prepared by a directed ortho metallation reaction (J. Org. Chem. 20001, 66, 3662-3670). In this case, the compound of formula (V) is prepared by reacting a compound of formula (VII)

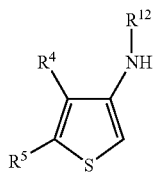

(VII)

where $R^4$ and $R^5$ are as defined in relation to formula (I) and $R^{12}$ is as defined in relation to formula (III), with a lithiating agent, such as N-butyl lithium, and subsequently with a formylating agent, such as a compound of formula (VIII)

(VIII)

where $R^9$ and $R^{10}$ are alkyl groups and in particular lower alkyl groups of 1 to 4 carbon atoms, such as methyl. Reaction with the lithiating agent is suitably effected in an organic solvent such as tetrahydrofuran (THF), at low temperatures for example of from −100° to 0° C. and preferably from −80° to −10° C. The subsequent addition of the formylating agent is suitably also effected at low temperatures, but in this case, temperatures of from −20° to 0° C. are adequate.

Compounds of formula (VII) are suitably prepared by subjecting a compound of formula (IX)

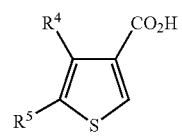

(IX)

where $R^4$ and $R^5$ are as defined above in relation to formula (I), to a Curtius rearrangement reaction, in the presence of an alcohol of formula $R^{14}OH$ where $R^{14}$ is as defined in relation to formula (ii). In this reaction, the compound of formula (IX) is reacted with diphenylphosphorylazide of formula (X)

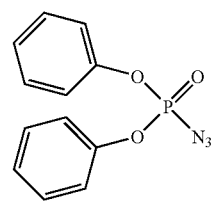

(X)

to convert the acid group to a carbonyl azide, which is thermally decomposed to the desired amide via an isocyanate. Suitable reaction conditions are illustrated hereinafter. The reaction is suitably effected in the presence of a base such as triethylamine.

Compounds of formula (IX) are suitably prepared by oxidation of a compound of formula (XI)

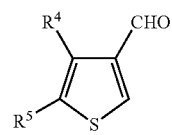

(XI)

where $R^4$ and $R^5$ are as defined in relation to formula (I) for example using an oxidising agent such as potassium permanganate in the presence of a base such as an alkali metal hydroxide such as sodium hydroxide. The reaction is suitably effected in an aqueous solvent at moderate temperatures for example of from 10 to 80° C. and preferably at about 40° C.

Compounds of formula (XI) where $R^4$ and $R^5$ are halogen can be prepared by halogenation of compounds of formula (XII)

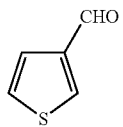
(XII)

Suitably this is effected using a halogenating agent such as chlorine and aluminium trichloride, in an organic solvent such as dichloromethane.

Compounds of formula (II), (III), (V) and (VII) are novel and form further aspects of the invention.

Compounds of formula (IV), (VI), (VIII), (IX), (X), (XI) and (XII) are known compounds or they can be prepared from known compounds by conventional methods.

Compounds of formula (I) are suitably used in the production of pharmaceutical compounds and in particular, compounds with glycogen phosphorylase activity as described in WO 02/20530 and EP-A-1088824.

Thus in a further aspect, the invention provides a method as described above, for the production of a compound of formula (I) where $R^6$ is hydrogen, and further comprising reacting the compound of formula (I) obtained with an amine of formula (XIII),

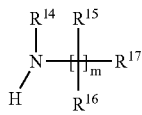
(XIII)

where $R^{14}$ is selected from hydrogen and $C_{1-8}$alkyl, m is an integer of from 0 to 4, each $R^{15}$ is the same or different and is selected from hydrogen, halo, nitro, cyano, hydroxy, amino, carboxy, carbamoyl, mercapto, sulphamoyl, ureido, $C_{1-6}$alkyl, $C_{2-6}$alkenyl, $C_{2-6}$alkyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$-alkanoylamino, N-($C_{1-6}$alkyl)carbamoyl, N,N-($C_{1-4}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, $C_{3-8}$cycloalkyl, $C_{3-8}$cycloalkyl$C_{1-6}$alkyl, aryl, aryl$C_{1-6}$alkyl, heterocyclic group and (heterocyclic group)$C_{1-6}$-alkyl; wherein $R^{15}$ may be optionally substituted on carbon by one or more groups selected from P and wherein if said heterocyclic group contains an —NH— moiety that nitrogen may be optionally substituted by a group selected from R;

each $R^{16}$ is the same or different and is selected from hydrogen and $C_{1-6}$alkyl;

$R^{17}$ is selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-4}$alkyl)$_2$carbamoyl, N-($C_{1-6}$alkyl)-N-($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, sulphamoylamino, N-($C_{1-6}$alkyl)sulphamoylamino, N,N-($C_{1-6}$alkyl)$_2$sulphamoylamino, $C_{1-6}$alkylsulphonylamino, $C_{1-6}$alkylsulphonylaminocarbonyl, $C_{1-6}$alkylsulphonyl-N-($C_{1-6}$alkyl)amino and a group -E-F-G-H;

wherein E and G are independently selected from a direct bond, —O—, —S—, —SO—, —SO$_2$—, —OC(O)—, —C(O)O—, —C(O)—, NR$^a$—, —NR$^a$C(O)—, —C(O)NR$^a$—, —SO$_2$NR$^a$—, —NR$^a$SO$_2$—, —NR$^a$C(O)NR$^b$—, OC(O)NR$^a$—, —NR$^a$C(O)O—, —NR$^a$SO$_2$NR$^b$—, —SO$_2$NR$^a$C(O)— and —C(O)NR$^a$SO$_2$—; wherein R$^a$ and R$^b$ are independently selected from hydrogen or $C_{1-6}$alkyl which is optionally substituted by a group V;

F is $C_{1-6}$alkylene optionally substituted by one or more Q or a direct bond;

H is selected from aryl, $C_{3-8}$cycloalkyl and heterocyclic group; wherein H may be optionally substituted on carbon by one or more groups selected from S and wherein if said heterocyclic group contains an —NH— moiety that nitrogen may be optionally substituted by a group selected from T;

P, S and Q are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$-alkyl)$_2$carbamoyl, N-($C_{1-6}$alkyl)-N-($C_{1-6}$ alkoxy)carbamoyl, $C_{1-6}$alkylS(O)$_a$ wherein a is 0 to 2, $C_{1-6}$-alkoxycarbonyl, $C_{1-6}$alkoxycarbonylamino, N-($C_{1-6}$-alkyl)sulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, $C_{3-8}$cycloalkyl, aryl and heterocyclic group; wherein P, S and Q may be optionally and independently substituted on carbon by one or more groups selected from V and wherein if said heterocyclic group contains an —NH— moiety that nitrogen may be optionally substituted by a group selected from U;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

R, T and U are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, phenyl, benzyl, benzyloxycarbonyl, benzoyl and phenylsulphonyl wherein R, T and U may be optionally and independently substituted on carbon by one or more groups selected from V;

to produce a compound of formula (XIV)

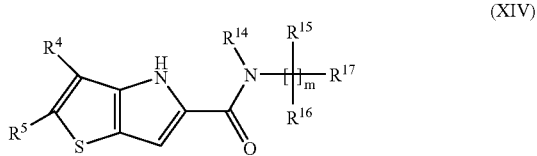

where $R^4$, $R^5$, $R^{15}$, $R^{16}$, $R^{17}$ and m are as defined above, or a pharmaceutically acceptable salt or an in viva hydrolysable ester thereof.

Particular examples of compounds of formula (XIV) are compounds where $R^{14}$ is hydrogen, as described in WO 02/20530. For instance, suitable compounds of formula (XIV) are compounds where $R^4$ and $R^5$ are as defined above, $R^{14}$ is hydrogen, m is 0 and $R^{17}$ is a group -E-F-G-H;

wherein E, P and G are each a direct bond;

H is a $C_{3-12}$cycloalkyl which is optionally fused to a benz ring wherein H may be optionally substituted on carbon by one or more groups S which are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$-alkyl)$_2$amino, $C_{1-6}$-alkanoylamino, N-($C_{1-6}$alkyl)carbamoyl, N,N-($C_{1-6}$alkyl)$_2$carbamoyl, N-($C_{1-6}$alkyl)-N-($C_{1-6}$alkoxy)carbamoyl, $C_{1-6}$alkylS(O)$_a$ wherein a is 0 to 2, $C_{1-6}$-alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{1-6}$-alkylsulphonyl-N-($C_{1-6}$alkyl)amino, $C_{3-8}$cycloalkyl, aryl and heterocyclic groups; wherein S may be optionally substituted on carbon by one or more groups selected from V;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl; N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

or a pharmaceutically acceptable salt thereof.

Other suitable compounds of formula (XIV) are compounds where $R^4$ and $R^5$ are as defined above, $R^{14}$ is hydrogen, m is 0, and $R^{17}$ is a group -E-F-G-H;

wherein E, F and G are each a direct bond; and

H is a cyclic amide of formula

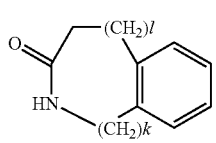

in which the point of attachment is the carbon atom adjacent to the carbonyl group, k is 0, 1 or 2 and 1 is 0, 1 or 2 such that the sum of (k+1) is 1, 2 or 3 and wherein one of the carbon atoms governed by k or l may be replaced by sulphur and wherein H is optionally substituted on the carbon atom adjacent to the aromatic ring by a group selected from S and may be independently optionally substituted on nitrogen by a group selected from T;

S is selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, N-($C_{1-6}$alkyl)-N-($C_{1-6}$alkoxy)carbamoyl, $C_{1-6}$-alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, $C_{3-8}$cycloalkyl, aryl and heterocyclic group; wherein S may be optionally and independently substituted on carbon by one or more groups selected from V and wherein if said heterocyclic group contains an —NH— moiety that nitrogen may be optionally substituted by a group selected from U;

T and U are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, phenyl, benzyl, benzyloxycarbonyl, benzoyl and phenylsulphonyl wherein R, T and U may be optionally and independently substituted on carbon by one or more groups selected from V;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl and 4-hydroxypiperidinocarbonyl;

or a pharmaceutically acceptable salt or an in vivo hydrolysable ester thereof.

Yet further examples of compounds of formula (XIV) are compounds where $R^{14}$ is hydrogen, and wherein $R^4$ and $R^5$ are independently selected from hydrogen, halo or $C_{1-6}$alkyl. m is 1; $R^{15}$ is hydrogen or aryl$C_{1-6}$alkyl, $R^{16}$ is hydrogen or $C_{1-6}$alkyl, and $R^{17}$ is selected from a group -E-F-G-H;

wherein E, F and G are each a direct bond;

H is an unsaturated five membered heterocyclic group containing at least one nitrogen atom and one or two ring atoms selected from oxygen and sulphur and wherein H may be optionally substituted on carbon by one or more groups S which are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, N-($C_{1-6}$alkyl)-N-($C_{1-6}$alkoxy)carbamoyl, $C_{1-6}$ alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, $C_{3-8}$cycloalkyl and aryl groups;

or a pharmaceutically acceptable salt thereof.

Other particular examples include compounds of formula (XIV) where $R^{14}$ is hydrogen, $R^4$ and $R^5$ are independently selected from hydrogen, halo or $C_{1-6}$alkyl.

m is 0; and $R^{17}$ is a group -E-F-G-H;
wherein E is a direct bond;
F is methylene;
wherein G is —C(O)$NR^a$—, wherein $R^a$ is selected from hydrogen or $C_{1-6}$alkyl which is optionally substituted by a group V;
H is aryl which may be optionally substituted on carbon by one or more groups selected from S;
S is selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$-alkoxy, $C_{1-6}$-alkanoyl, $C_{1-6}$-alkanoyloxy, N-($C_{1-6}$ alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, N-($C_{1-6}$alkyl)-N-($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, $C_{3-8}$cycloalkyl, aryl and heterocyclic group; wherein S may be optionally and independently substituted on carbon by one or more groups selected from V;
V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

or a pharmaceutically acceptable salt thereof.

Other particular compounds of formula (XIV) are compounds where the group

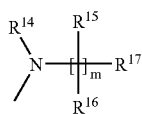

is a group of sub-formula (ii)

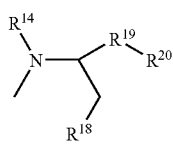

(ii)

where $R^{14}$ is as defined above, $R^{18}$ is aryl, substituted aryl, heteroaryl, or substituted heteroaryl, $R^{19}$ is a bond or a group —CH(OH)—, and $R^{20}$ is a group —C(=O)-A or a group —CH(OH)—C(=O)-A in which A is $NR^aR^d$, —$NR^a$CH$_2$CH$_2$O$R^a$, or

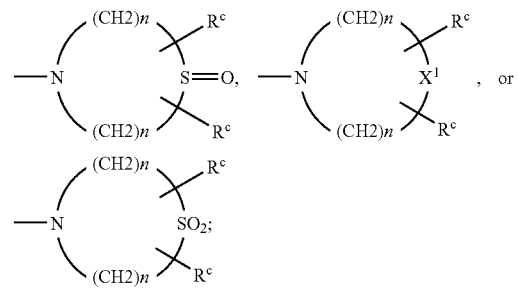

each $R^a$ and $R^b$ is independently hydrogen or —$C_1$-$C_8$alkyl;
each $R^d$ is independently hydrogen, $C_1$-$C_8$alkyl, $C_1$-$C_8$alkoxy, aryl, substituted aryl, heteroaryl, or substituted heteroaryl;
each $R^c$ is independently hydrogen, —C(=O)$OR^a$, —$OR^a$, —$SR^a$, or —$NR^aR^a$; and each n is independently 1-3, and $X^1$ is $NR^a$, —CH$_2$—, O or S.

Examples of substituents for aryl and heteroaryl groups Q and $R^d$ include halogen, $C_{1-8}$alkoxy, $C_{1-8}$alkyl, trifluoromethyl, amino, mono or di-($C_{1-8}$alkyl)amino, nitro, cyano, carboxy or $C_{1-8}$alkyl esters thereof.

The invention will now be particularly described by way of example, in which, unless stated otherwise:

(i) temperatures are given in degrees Celsius (° C.); operations were carried out at room or ambient temperature, that is, at a temperature in the range of 18-25° C. and under an atmosphere of an inert gas such as argon;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) yields are given for illustration only and are not necessarily those which can be obtained by diligent process development; preparations were repeated if more material was required;

(vi) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent or other solvents (where indicated in the text) including deuterated chloroform CDCl$_3$;

(vii) chemical symbols have their usual meanings; SI units and symbols are used;

(viii) reduced pressures are given as absolute pressures in Pascals (Pa); elevated pressures are given as gauge pressures in bars;

(ix) solvent ratios are given in volume: volume (v/v) terms;

(x) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported and unless otherwise stated the value quoted is M-H)$^-$;

The following abbreviations are used:
DMSO=dimethylsulfoxide
DCM=dichloromethane
THF is tetrahydrofuran
HPLC is high performance liquid chromatography
DMF is dimethylformamide
THF is tetrahydrofuran

EXAMPLE 1

Step 1

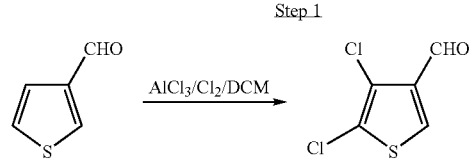

Thiophene-3-carbaldehyde (11.2 g, 0.1M) was dissolved in dichloromethane (400 ml) and cooled to 5° C. Aluminium chloride (33.25 g, 0.25M) was then added in portions so that the temperature did not rise above 10° C. After the addition was complete the temperature was allowed to rise to 15° C. and chlorine gas slowly bubbled into the reaction mixture. The temperature was maintained between 15 and 20° C. with ice/water cooling and the reaction followed by HPLC until the mixture contained >70% of 4,5-dichlorothiophene-3-carbaldehyde.

The reaction mixture was poured into ice water (1000 ml) and the organic layer separated. The aqueous was extracted with further portions of dichloromethane (3×200 ml) and the combined extracts washed with saturated sodium bicarbonate, water and brine, dried over magnesium sulphate and evaporated to give a dark oil, which crystallised on standing. Purification by recrystallisation from hexane gave 4,5-dichlorothiophene-3-carbaldehyde as light brown needles (14 g, 78%). $^1$H NMR (300 MHz, d$^6$-DMSO) 9.9 (s, 1H), 8.0 (s, 1H)

Step 2

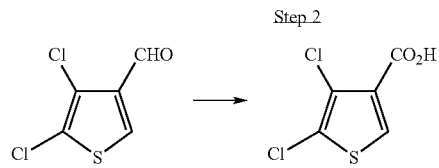

NaOH (0.47 g) was dissolved in H$_2$O (8 ml) and 4,5-dichlorothiophene-3-carbaldehyde from step 1 (1.42 g) added in one portion giving a suspension. KMnO$_4$ (1.24 g) was added portionwise over approximately 25 minutes whilst heating the reaction suspension in a water bath at 40° C. After complete addition the water bath temperature was raised to 50° C. for a further 15 minutes stirring.

Without cooling the brown precipitate was filtered off (nylon filter) and washed with H$_2$O. The resultant pale yellow clear solution was acidified with concentrated aqueous hydrochloric acid to give a thick white suspension. The white solid was filtered off and washed with H$_2$O. The solid was dissolved in a mixture of ethyl acetate and dichloromethane, dried over MgSO$_4$, filtered and evaporated under reduced pressure to leave the desired product, 4,5-dichlorothiophene-3-carboxylic acid as a white solid (1.34 g). Further product was extracted from the aqueous mother liquors using dichloromethane. After drying over Na$_2$SO$_4$, filtration and evaporation under reduced pressure, an additional 0.19 g of the desired 4,5-dichlorothiophene-3-carboxylic acid was obtained as a white solid. $^1$H NMR (300 MHz, d$^6$-DMSO) 13.23 (br s, 1H), 8.33 (s, 1H); ESP$^-$ 195.12

Step 3

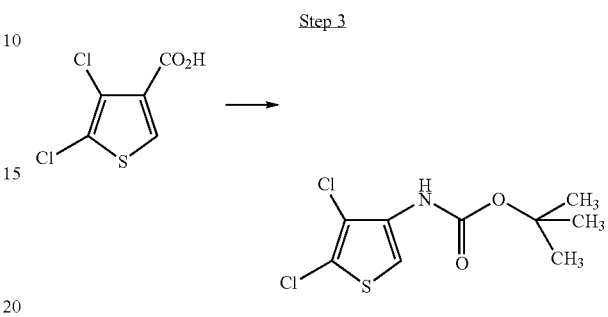

Under argon 4,5-dichlorothiophene-3-carboxylic acid (10.91 g) was dissolved in warm dry tertiary butanol (60 ml) and triethylamine (7.76 ml) added followed by diphenylphosphoryl azide (DPPA) (11.99 ml). The mixture was then heated slowly to reflux and refluxed for about 12 hours. On cooling the reaction mixture was poured into H$_2$O (~300 ml). The resultant dark suspension was filtered, and the solid was washed with H$_2$O then dried under suction to a brown powder. This was dissolved in diethyl ether and the solution dried over MgSO$_4$, filtered and evaporated. Chromatography on silica gel (eluent gradient—isohexane to CH$_2$Cl$_2$) gave tert-butyl (4,5-dichloro-3-thienyl)carbamate as a pale yellow solid. Yield 12.05 g (78%). $^1$H NMR (300 MHz, CDCl$_3$) 7.30 (br s, 1H), 6.72 (br s, 1H), 1.51 (s, 9H)

Step 4

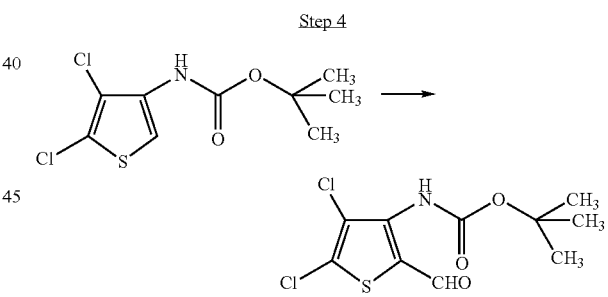

The product from step 3 (445 mg) was dissolved in tetrahydrofuran (THF) under an argon atmosphere, and cooled in a dry ice/acetone bath. n-Butyl lithium (1.6M in hexane) (2.5 ml) was added dropwise and the mixture left at this temperature for 35 minutes then allowed to warm to −10° C. (external bath temperature) over ~15 minutes. Dimethylformamide (0.25 ml) was then added dropwise and the temperature held at 10° C. for 30 minutes, before being allowed to warm to room temperature. It was kept at this temperature with stirring overnight.

Saturated aqueous sodium chloride solution was then added, and the mixture then partitioned between ethyl acetate and water. The organic phase was dried over MgSO$_4$, filtered and evaporated to gave a pale brown solid Chromatography on silica gel (eluent gradient—isohexane to CH$_2$Cl$_2$) gave tert-butyl (4,5-dichloro-2-formyl-3-thienyl)

carbamate as a pale yellow solid. Yield 0.31 g (63%). $^1$H NMR (300 MHz, CDCl$_3$) 10.01 (s, 1H), 6.83 (br s, 1H), 1.52 (s, 9H); ESP$^-$ 294.07 silica gel (eluent gradient—isohexane to CH$_2$Cl$_2$ then to Et$_2$O: CH$_2$Cl$_2$ (3:97)) gave the methyl N-acetyl-N-(4,5-dichloro-2-formyl-3-thienyl)glycinate as a clear yellow oil (34 mg). $^1$H NMR (300 MHz, CDCl$_3$) 10.22 (s, 1H), 5.00 (d, 1H), 3.75 (d, 1H), 3.72 (s, 3H), 1.99 (s, 3H)

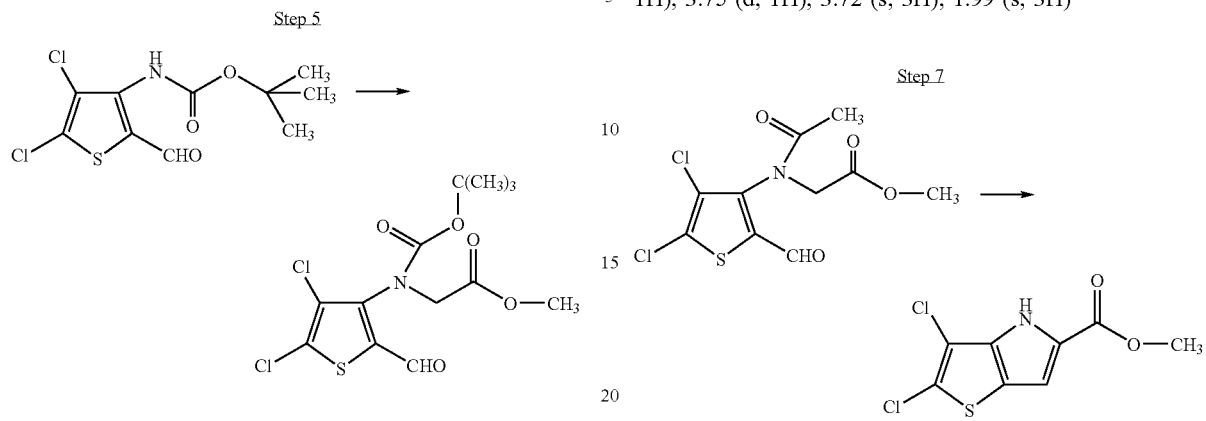

The product from step 4 (300 mg) was dissolved in dry DMF (2 ml) under an argon atmosphere, and KHCO$_3$ (102 mg) was added followed by methyl bromoacetate (96 μl). The mixture was then heated to 60° C., for 3½ hours. After stirring overnight at room temperature, further KHCO$_3$ (51 mg) and methyl bromoacetate (48 μl) were added and the mixture heated at 60° C. for a further 1 hour 30 minutes.

The reaction mixture was then partitioned between ethylacetate and H$_2$O. The organic layer was dried over MgSO$_4$, filtered and evaporated to a clear, orange oil. Chromatography on silica gel (eluent gradient—isohexane to CH$_2$Cl$_2$ then to Et$_2$O) gave methyl N-(tert-butoxycarbonyl)-N-(4,5-dichloro-2-formyl-3-thienyl)glycinate as a clear yellow oil (0.42 g). $^1$H NMR (300 MHz, CDCl$_3$) (exists as 2:1 mixture of rotamers) 10.13 (s, 1H), 4.78 (d, 1H), 3.87 (d, 1H), 3.72 (s, 3H), 1.38 (s, 9H) (major rotamer); 10.05 (s, 1H), 4.58 (d, 1H), 3.87 (d, 1H), 3.75 (s, 3H), 1.50 (s, 9H) (minor rotamer)

The product of step 6 (103 mg) under an argon atmosphere and K$_2$CO$_3$ (70 mg) were mixed together and dry DMF (1 ml) added. The suspension quickly went red. After 2 hrs at room temperature, the temperature was raised to 60° C. for 165 minutes. The reaction mixture was cooled to room temperature and stirred overnight.

The product was then worked-up using procedures as described in step 6, and the organic phase dried over Na$_2$SO$_4$. Chromatography on silica gel (eluent gradient—isohexane to CH$_2$Cl$_2$ then to Et$_2$O) gave methyl 2,3-dichloro-4H-thieno[3,2-b]pyrrole-5-carboxylate as a white solid (37 mg)(45%). $^1$H NMR (300 MHz, d$^6$-DMSO) 12.86 (br s, 1H), 7.20 (s, 1H), 3.86 (s, 3H); ESP$^-$ 248.04

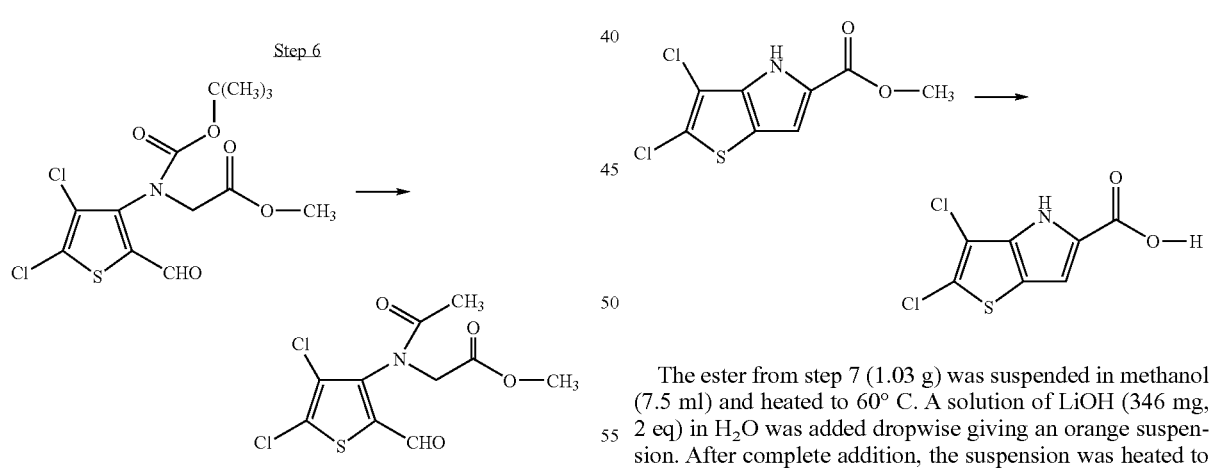

Under an argon atmosphere, the product of step 5 (746 mg) was dissolved in acetic acid (5 ml) and acetic anhydride (0.41 ml) added. After heating for 21 hours at 120° C., the reaction mixture was evaporated under reduced pressure, and the residue partitioned between CH$_2$Cl$_2$ and aqueous sodium bicarbonate solution. The organic layer was dried over MgSO$_4$, filtered and evaporated under reduced pressure.

The organic layer was dried over MgSO$_4$, filtered and evaporated under reduced pressure. Chromatography on The ester from step 7 (1.03 g) was suspended in methanol (7.5 ml) and heated to 60° C. A solution of LiOH (346 mg, 2 eq) in H$_2$O was added dropwise giving an orange suspension. After complete addition, the suspension was heated to reflux for 1 hour, whereupon it had become a clear orange solution. The reaction mixture was concentrated to almost dryness under reduced pressure, then acidified with 2M aqueous hydrochoric acid, and extracted with ethyl acetate (twice). The ethyl acetate layer was dried over MgSO$_4$, filtered and evaporated under reduced pressure. Residual traces of MeOH were removed by azeotroping with toluene to leave the desired 2,3-dichloro-4H-thieno[3,2-b]pyrrole-5-carboxylic acid as an off white solid (0.98 g, 100%).

$^1$H NMR (400 MHz, d$^6$-DMSO) 12.79 (or s, 1H), 12.63 (br s, 1H), 7.09 (s, 1H), 3.86; ESP$^-$ 234.21

The invention claimed is:

1. A process for preparing a compound of formula (I)

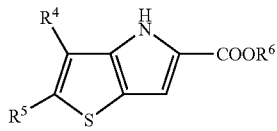

where $R^4$ and $R^5$ are independently selected from halo; and $R^6$ is hydrogen or a protecting group, which process comprises cyclisation of a compound of formula (II)

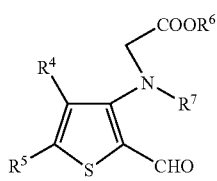

where $R^4$, $R^5$ and $R^6$ are as defined in relation to formula (I), and $R^7$ is a nitrogen protecting group; and removing the group $R^7$;

and thereafter optionally removing any protecting group $R^6$.

2. A process according to claim 1 wherein $R^7$ is a group of sub-formula (i)

where $R^8$ is a straight chain alkyl group of from 1 to 6 carbon atoms.

3. A process according to claim 1, for preparing a compound of formula (I) where $R^6$ is hydrogen, wherein the method further comprises the step of reacting the compound of formula (I) obtained with an amine of formula (XIII)

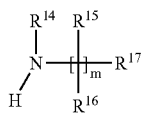

where $R^{14}$ is selected from hydrogen or $C_{1-8}$alkyl, m is an integer of from 0 to 4, each $R^{15}$ is the same or different and is selected from hydrogen, halo, nitro, cyano, hydroxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-4}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, $C_{3-8}$cycloalkyl, $C_{3-8}$cycloalkylC$_{1-6}$alkyl, aryl, arylC$_{1-6}$alkyl, heterocyclic group and (heterocyclic group)C$_{1-6}$alkyl; wherein $R^{15}$ may be optionally substituted on carbon by one or more groups selected from P and wherein if said heterocyclic group contains an —NH— moiety that nitrogen may be optionally substituted by a group selected from R;

each $R^{16}$ is the same or different and is selected from is hydrogen or $C_{1-6}$alkyl;

$R^{17}$ is selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-4}$alkyl)$_2$carbamoyl, N-($C_{1-6}$alkyl)-N-($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, sulphamoylamino, N-($C_{1-6}$alkyl)sulphamoylamino, N,N-($C_{1-6}$alkyl)$_2$sulphamoylamino, $C_{1-6}$alkylsulphonylamino, $C_{1-6}$alkylsulphonylaminocarbonyl, $C_{1-6}$alkylsulphonyl-N-($C_{1-6}$alkyl)amino and a group -E-F-G-H;

wherein E and G are independently selected from a direct bond, —O—, —S—, —SO—, —SO$_2$—, —OC(O)—, —C(O)O—, —C(O)—, —NR$^a$—, —N$^a$C(O)—, C(O)NR$^a$—, —SO$_2$NR$^a$—, —NR$^a$SO$_2$—, —NR$^a$C(O)NR$^b$—, —OC(O)NR$^a$—, —NR$^a$C(O)O—, —NR$^a$SO$_2$NR$^b$—, —SO$_2$NR$^a$C(O)— and —C(O)NR$^a$SO$_2$—; wherein $R^a$ and $R^b$ are independently selected from hydrogen or $C_{1-6}$alkyl which is optionally substituted by a group V;

F is $C_{1-6}$alkylene optionally substituted by one or more Q or a direct bond;

H is selected from aryl, $C_{3-8}$cycloalkyl and heterocyclic groups; wherein H may be optionally substituted on carbon by one or more groups selected from S and wherein if said heterocyclic group contains an —NH— moiety that nitrogen may be optionally substituted by a group selected from T;

P, S and Q are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, N-($C_{1-6}$alkyl)-N-($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N-($C_{1-6}$alkyl)sulphamoyl, N,N-($C_{1-6}$alkyl)$_2$sulphamoyl, $C_{1-6}$alkylsulphonylamino, $C_{1-6}$alkylsulphonyl-N-($C_{1-6}$alkyl)amino, $C_{3-8}$cycloalkyl, aryl and heterocyclic group; wherein P, S and Q may be optionally and independently substituted on carbon by one or more groups selected from V and wherein if said heterocyclic group contains an —NH— moiety that nitrogen may be optionally substituted by a group selected from U;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

R, T and U are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, phenyl, benzyl, benzyloxycarbonyl, benzoyl and phenylsulphonyl wherein R, T and U may be optionally and independently substituted on carbon by one or more groups selected from V;

producing a compound of formula (XIV)

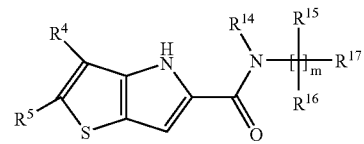

(XIV)

where $R^4$, $R^5$, $R^{15}$, $R^{16}$, $R^{17}$ and m are as defined above, or a pharmaceutically acceptable salt or an in vivo hydrolysable ester thereof.

* * * * *